(12) United States Patent
Lunn et al.

(10) Patent No.: US 8,066,677 B2
(45) Date of Patent: Nov. 29, 2011

(54) RAPID EXCHANGE CATHETER WITH TEAR RESISTANT GUIDEWIRE SHAFT

(75) Inventors: Peter Lunn, Beverly, MA (US); Matthew Spurchise, Peabody, MA (US)

(73) Assignee: Medtronic Vascular, Inc, Santa Rosa, CA (US)

( * ) Notice: Subject to any disclaimer, the term of this patent is extended or adjusted under 35 U.S.C. 154(b) by 158 days.

(21) Appl. No.: 12/052,892

(22) Filed: Mar. 21, 2008

(65) Prior Publication Data
US 2009/0240206 A1  Sep. 24, 2009

(51) Int. Cl.
*A61M 5/32* (2006.01)
*A61M 25/00* (2006.01)

(52) U.S. Cl. .................................. 604/175; 604/528

(58) Field of Classification Search .......... 604/158–163, 604/174
See application file for complete search history.

(56) References Cited

U.S. PATENT DOCUMENTS

| | | | |
|---|---|---|---|
| 5,217,482 A | 6/1993 | Keith | |
| 5,306,261 A | 4/1994 | Alliger et al. | |
| 5,336,184 A | 8/1994 | Teirstein | |
| 5,690,642 A | 11/1997 | Osborne et al. | |
| 5,814,061 A | 9/1998 | Osborne et al. | |
| 6,059,769 A | 5/2000 | Lunn et al. | |
| 6,248,092 B1 | 6/2001 | Miraki et al. | |
| 6,371,961 B1 | 4/2002 | Osborne et al. | |
| 6,482,184 B1* | 11/2002 | Christensen et al. | 604/174 |
| 7,208,001 B2 | 4/2007 | Coyle et al. | |
| 7,273,486 B2 | 9/2007 | Coyle et al. | |
| 2007/0106211 A1 | 5/2007 | Provost-Tine et al. | |
| 2007/0191812 A1* | 8/2007 | Nishide et al. | 604/523 |

FOREIGN PATENT DOCUMENTS

| | | |
|---|---|---|
| EP | 0611582 | 8/1994 |
| WO | WO95/32756 | 12/1995 |
| WO | WO02/26309 | 4/2002 |

OTHER PUBLICATIONS

International Search Report in PCT/US2009/035808.

* cited by examiner

*Primary Examiner* — Kevin C Sirmons
*Assistant Examiner* — Imani Hayman (57) ABSTRACT

A rapid exchange-type catheter for aspiration of embolic debris from a blood vessel includes an elongate aspiration tube and a relatively short guidewire tube mounted beside a distalmost portion of the aspiration tube. A proximal portion of the guidewire tube defines a strain relief segment. In one embodiment, the strain relief segment is formed detached from the aspiration tube. In another embodiment, the strain relief segment is minimally attached to the aspiration tube and becomes detached from the aspiration tube when a sufficient transverse force is applied to urge the guidewire tube away from the aspiration tube.

11 Claims, 7 Drawing Sheets

RAPID EXCHANGE CATHETER WITH TEAR RESISTANT GUIDEWIRE SHAFT

FIELD OF THE INVENTION

The present invention relates to aspiration catheters for aspiration of thrombotic, atherosclerotic or other particulate embolic debris from a blood vessel, the apparatus being particularly well suited for aspiration within saphenous vein grafts, arteries in the heart, head and neck, and similar vessels.

BACKGROUND OF THE INVENTION

Human blood vessels often become occluded or completely blocked by plaque, thrombi, other deposits, emboli or other substances, which reduce the blood carrying capacity of the vessel. Should the blockage occur at a critical place in the circulatory system, serious and permanent injury, or even death, can occur. To prevent this, some form of medical intervention is usually performed when significant occlusion is detected.

A serious example of vascular occlusion is coronary artery disease, which is a common disorder in developed countries and is the leading cause of death in the United States. Damage to or malfunction of the heart is caused by narrowing or blockage of the coronary arteries that supply blood to the heart. The coronary arteries are first narrowed and may eventually be completely blocked by plaque (atherosclerosis), and the condition may further be complicated by the formation of thrombi (blood clots) on roughened surfaces of, or in eddy currents caused by the plaques. Myocardial infarction can result from coronary atherosclerosis, especially from an occlusive or near-occlusive thrombus overlying or adjacent to the atherosclerotic plaque, leading to ischemia and/or death of portions of the heart muscle. Thrombi and other particulates also can break away from arterial stenoses, and this debris can migrate downstream to cause distal embolization.

Various types of intervention techniques have been developed to facilitate the reduction or removal of a blockage in a blood vessel, allowing increased blood flow through the vessel. One technique for treating stenosis or occlusion of a blood vessel is balloon angioplasty wherein a balloon catheter is inserted into the narrowed or blocked area, and the balloon is inflated to expand the constricted area. Other types of interventions include atherectomy, deployment of stents, local infusion of specific medication, and bypass surgery. Each of these methods is not without the risk of embolism caused by the dislodgement of the blocking material, which may then move downstream.

Often, more than one interventional catheter is used during a procedure, such as to change the size of the balloon being used or to introduce additional devices into the system to aid with the procedure, including stent delivery catheters and aspiration catheters. In such situations, the catheters are generally inserted into the patient's cardiovascular system with the assistance of a guidewire. For example, a guidewire is introduced into the patient, steered through the tortuous pathways of the cardiovascular system, and positioned across an intended treatment location. Various catheters having a lumen adapted to receive the guidewire may then be introduced into and removed from the patient along the guidewire, thereby decreasing the time needed to complete a procedure.

Many techniques exist for preventing the release of thrombotic or embolic particles into the bloodstream during such a procedure. Common among these techniques is introduction of an occlusive device or a filter downstream of the treatment area to capture these embolic or thrombotic particles. The particles may then be removed from the vessel with the withdrawal of the occlusive or filtering device. In another common technique, the particles may be removed by an aspiration catheter prior to the withdrawal of these devices. Aspiration catheters have also been found useful in removing thrombus prior to crossing underlying atherosclerotic plaque with guidewires and/or treatment catheters. Such preliminary removal of thrombus makes it easier to cross the stenosis and less likely to release thrombo-embolic particles into the bloodstream during the procedure.

An aspiration catheter may be designed such that a guidewire is contained within the aspiration lumen as the catheter is advanced there over, or the aspiration catheter may include a dedicated guidewire lumen extending along substantially the entire length of the aspiration catheter such that the guidewire is disposed therein as the catheter is advanced through a body lumen. Such dual-lumen catheters having an aspiration lumen and a guidewire lumen may be constructed in a variety of ways including relatively simple profile extrusions, more complex assemblies of different tubular components, and combinations of these two methods.

Dual-lumen profile extrusions can have parallel round lumens surrounded by relatively uniform walls, resulting in a non-circular, generally figure-eight shaped transverse cross section. Alternatively, if a circular outer profile is desired, then dual-lumen profile extrusions can have parallel round lumens with non-uniform wall thicknesses or various other combinations of lumens having unequal sizes and non-round cross-sectional shapes such as D-shapes or crescent-shapes, as will be understood by one of skill in the field of cardiovascular catheters.

One of the important features of aspiration catheters is the ability to rapidly and efficiently aspirate even large embolic particles without the need to first break them into smaller sub-particles. This advantage is achieved, at least in part, by providing the catheter with an aspiration lumen having as large a cross sectional area as possible, given overall size constraints of the catheter design. In embodiments having an aspiration lumen that is crescent shaped or has another non-round shape, a relatively large cross-sectional area is preferably maintained to achieve rapid and efficient aspiration.

Aspiration catheters may also be of the so-called single operator or rapid exchange type. A rapid exchange aspiration catheter typically includes a tubular catheter shaft with an aspiration lumen extending the entire length thereof and a substantially shorter guidewire lumen extending along a distal portion of the catheter. As such, the guidewire is located outside of the aspiration catheter except for a short guidewire segment that extends within the guidewire lumen. Advantageously, a clinician is able to control both ends of the guidewire while the aspiration catheter is loaded or exchanged onto the guidewire, which may be already indwelling in the patient. The aspiration catheter is then advanced through the patient's vasculature with only a distal portion of the catheter riding on the guidewire.

Figure 1:
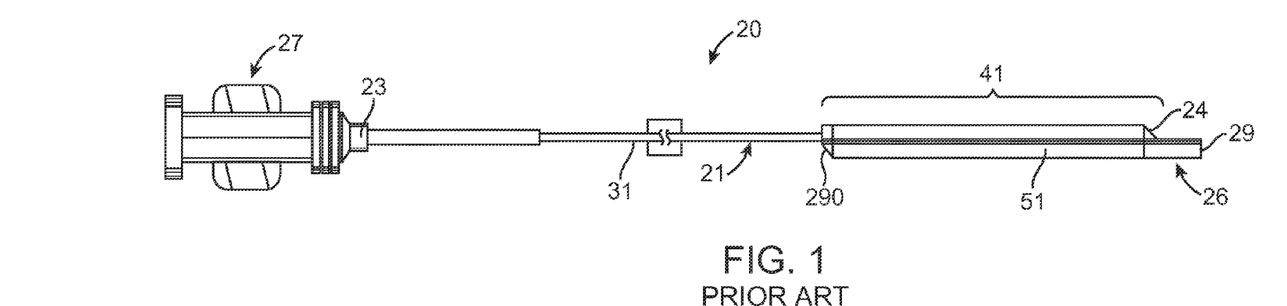
FIG. 1 is a side view of a prior art aspiration catheter.

Several types of aspiration catheters are disclosed in U.S. Patent Application Publication 2007/0106211 to Provost-Tine et al., which is incorporated by reference herein in its entirety. One of the aspiration catheters in the '211 publication is a rapid-exchange configuration, illustrated as FIG. 1 of the present application. FIG. 1 illustrates an aspiration catheter 20 suited for use in the treatment and removal of occlusions in blood vessels. Catheter 20 has a fitting 27 mounted at the proximal end in fluid communication with a proximal aspiration port 23. Catheter 20 includes an elongate tubular body 21 having a distal tip 26. Distal tip 26 can include a radiopaque marker (not shown) to aid in fluoroscopically locating tip 26 during insertion into the patient, and tip 26 is preferably soft to prevent damage to the patient's vasculature. Elongate tubular body 21 includes an aspiration tube 31 extending from fitting 27 to a location at or adjacent the distal end of tubular body 21. Aspiration tube 31 includes a tubular wall that defines an open aspiration lumen 12 (shown in FIG. 2), which extends the full length of tube 31. Aspiration lumen 12 fluidly connects aspiration port 23 disposed at or adjacent the proximal end of tubular body 21 with a distal fluid port 24 disposed at or adjacent the distal end of tubular body 21. A source (not shown) of partial vacuum or "negative pressure" may be connected to the luer adaptor of fitting 27 to aspirate blood and particulates through aspiration lumen 12 of catheter 20.

Catheter 20 further includes a dual lumen section 41 that is substantially shorter than the full length of catheter 20. Dual lumen section 41 includes a guidewire tube 51 that defines an open guidewire lumen 15 (shown in FIG. 2) sized and shaped to slidingly accept a medical guidewire therethrough. Guidewire tube 51 extends from an open proximal end 290 to an open distal end 29, alongside a distal portion of aspiration tube 31 such that aspiration lumen 12 and guidewire lumen 15 are in a parallel or side-by-side configuration. Dual lumen section 41 thus extends proximally from second fluid port 24 disposed at the distal end of aspiration tube 31 to open proximal end 290 of guidewire tube 51.

Figure 2:
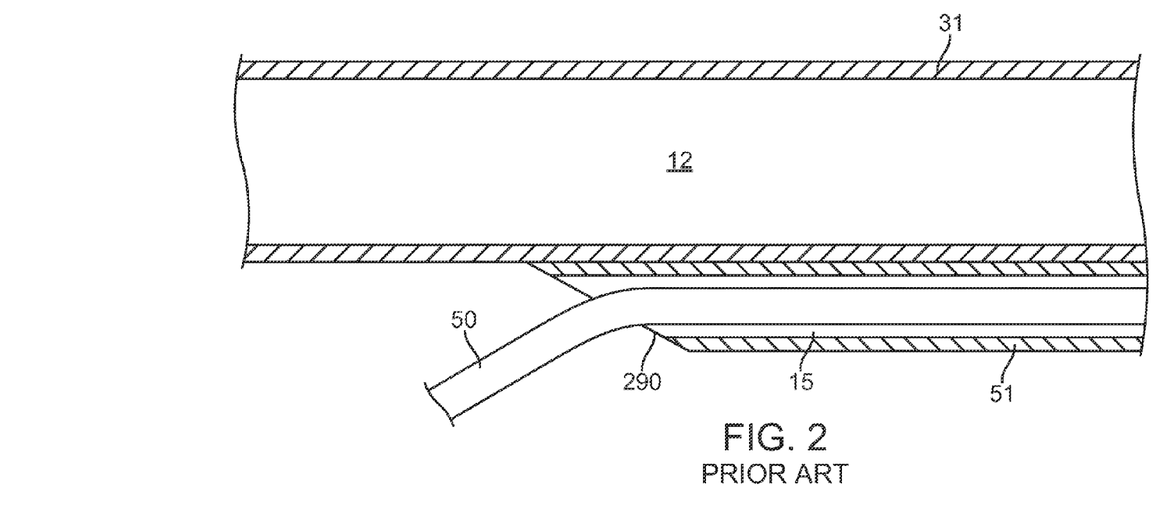
FIG. 2 is an enlarged longitudinal cross-sectional view of the proximal guidewire port of the aspiration catheter of FIG. 1, with a guidewire extending within the guidewire lumen.

FIG. 2 is an enlarged cross-sectional view of open proximal end 290 of guidewire tube 51, showing a guidewire 50 extending through guidewire lumen 15. As shown in FIG. 2, open proximal end 290, which may also be referred to as a proximal guidewire port, of guidewire tube 51 is attached to the outer surface of aspiration tube 31. When the proximal guidewire port is attached to the catheter shaft in this manner, forces applied in a transverse direction to separate the guidewire from the catheter may cause the guidewire to tear the wall of guidewire tube 51, starting from open proximal end 290. There is therefore a need for an improved aspiration catheter that avoids the above-described problem of the guidewire tearing the guidewire shaft.

BRIEF SUMMARY OF THE INVENTION

Embodiments of the present invention relate to an elongate aspiration catheter for removing particles from a blood vessel. The catheter includes an elongate aspiration tube having an aspiration lumen defined by an inner surface of the aspiration tube. The aspiration tube has a proximal port and a distal port fluidly connected via the aspiration lumen. The catheter also includes a guidewire tube disposed alongside and not extending proximally beyond a distal portion of the aspiration tube. The guidewire tube has a guidewire lumen defined by an inner surface of the guidewire tube and has a proximal end opening and a distal end opening that are connected via the guidewire lumen. The guidewire tube includes a distal portion secured to the distal portion of the aspiration tube and a proximal portion that defines a strain relief segment. When a transverse force is applied to urge the guidewire tube away from the aspiration tube, the strain relief segment is detached from the aspiration tube.

Embodiments of the present invention also relate to a method of making an aspiration catheter. An elongate, flexible first tube is provided, the first tube having a single lumen extending longitudinally therethrough. A flexible second tube is provided, the second tube having a lumen extending longitudinally therethrough and being open at proximal and distal ends thereof. The second tube is substantially shorter than the first tube. The second tube is secured beside a distalmost portion of the first tube such that a proximal portion of the second tube that is of a length that is 0.5-10% of a total length of the second tube forms a strain relief segment.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of an aspiration catheter, the invention may be used in any type of rapid exchange or single operator catheter device having a proximal guidewire port where it is deemed useful. In addition, although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Embodiments of the present invention are directed to a rapid-exchange aspiration catheter having an aspiration tube with an aspiration lumen extending therethrough and a substantially shorter guidewire tube having a guidewire lumen extending therethrough attached to a distal portion of the aspiration tube A short proximal portion of the guidewire tube defines a detached or detachable strain relief segment to prevent the above-described problem of the guidewire tearing the wall of the guidewire shaft. In embodiments of the present invention, forces applied in a transverse direction to separate the guidewire from the catheter are redirected by a strain relief segment to result in an attempt to peel the guidewire tube away from the aspiration tube rather than resulting in the guidewire tearing the wall of the guidewire tube. Accordingly, the incorporation of a strain relief segment at the proximal end of the guidewire tube improves the catheter's resistance to wall tearing because the force required to peel the guidewire tube away from the aspiration tube has been found to be several times the force required to tear the wall of the guidewire tube. Further explanation and details will now be described with reference to FIGS. 3-11.

Figure 3:
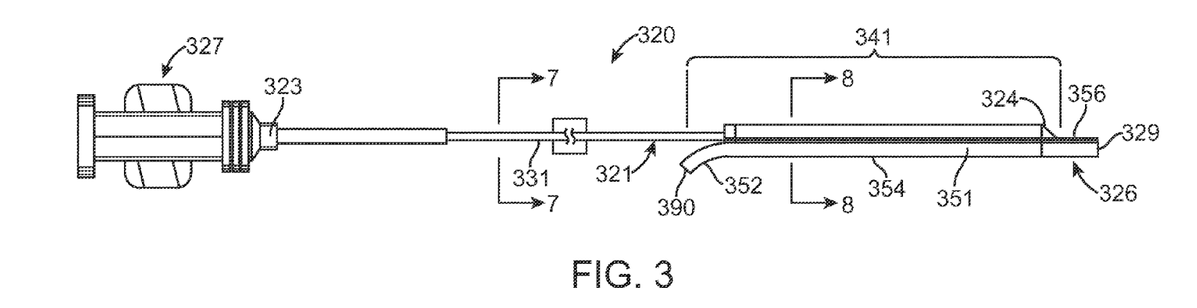
FIG. 3 is a side view of an aspiration catheter according to an embodiment of the present invention.

Before and/or after an interventional catheterization procedure has been performed and a stenosis has been removed or dilated, the treatment site may be aspirated to remove fluid and potentially embolic debris. FIG. 3 illustrates a rapid-exchange or single operator aspiration catheter 320 particularly suited for use in the treatment and removal of occlusions in blood vessels. Catheter 320 has an elongate tubular body 321 including an aspiration tube 331 and a substantially shorter guidewire tube 351 along a distal portion of catheter 320. Guidewire tube 351 includes a strain relief segment 352 at a proximal end thereof. In the present embodiment, strain relief segment 352 is a short portion of guidewire tube 351 that is detached from aspiration tube 331. Detached strain relief segment 352 prevents the above-described problem of the guidewire tearing the guidewire shaft. In an embodiment, strain relief segment 352 may be between 0.50 millimeters and one centimeter in length.

Mounted at the proximal end of catheter 320, a fitting 327 is in fluid communication with a proximal aspiration port 323. A source (not shown) of partial vacuum or "negative pressure" may be connected to the luer adaptor of fitting 327 to aspirate blood and particulates through an aspiration lumen 412, shown in FIG. 4, of catheter 320. Aspiration lumen 412 is unobstructed to provide efficient aspiration. A distal tip 326 is disposed at the distal end of elongate tubular body 321. Distal tip 326 can include a radiopaque marker (not shown) to aid in fluoroscopically locating tip 326 during insertion into the patient, and tip 326 is preferably soft to prevent damage to the patient's vasculature.

Aspiration tube 331 extends from fitting 327 to a location at or adjacent the distal end of tubular body 321. With additional reference to FIG. 4, aspiration tube 331 has a tubular wall that defines an open aspiration lumen 412, which extends the full length of aspiration tube 331. Aspiration lumen 412 fluidly connects a first aspiration port 323 disposed at or adjacent the proximal end of tubular body 321 with a second fluid port 324 disposed at or adjacent the distal end of tubular body 321. In the embodiment shown in FIG. 3, second fluid port 324 forms an oblique opening that faces away from guidewire tube 351. Optionally, fluid port 324 can form an opening that is orthogonal (not shown) to aspiration tube 331. Although not shown for sake of clarity in FIG. 4, aspiration catheter 320 is a laminated structure as described herein with respect to FIGS. 7-8. However, in another embodiment of the present invention, aspiration tube 331 and/or guidewire tube 351 may have another configuration, such as for example a single-layer tubular structure.

Catheter 320 further includes a dual lumen section 341 that is substantially shorter than the full length of catheter 320 where guidewire tube 351 is disposed adjacent to the distal portion of aspiration tube 331. With additional reference to FIG. 4, guidewire tube 351 has a tubular wall that defines a guidewire lumen 415, which extends the full length of guidewire tube 351 from open distal end 329 at catheter distal tip 326 to open proximal end 390 of guidewire tube 351. Guidewire lumen 415 is sized and shaped to slidingly accept a medical guidewire 450 therethrough. Guidewire tube 351 extends alongside a distal portion of aspiration tube 331 such that aspiration lumen 412 and guidewire lumen 415 are in a parallel or side-by-side configuration. Dual lumen section 341 thus proximally extends from second fluid port 324 disposed at the distal end of aspiration tube 331 to open proximal end 390 of guidewire tube 351. In various embodiments, dual lumen section 341 may be less than 10 cm in length or may proximally extend 30 cm or longer from distal tip 326.

During delivery of aspiration catheter 320, the proximal end of a medical guidewire 450 is inserted into open distal end 329 of guidewire lumen 415, and guidewire tube 351 is slidingly advanced over guidewire 450. Only a short portion, i.e., dual lumen section 341, of catheter 320 rides over guidewire 450, which remains in guidewire lumen 415 and does not enter aspiration lumen 412 of the aspiration catheter 320. Thus, single operator aspiration catheter 320 does not require an extra long guidewire or a guidewire extender and may be handled by only one clinician. Aspiration catheter 320 may be used with a medical guidewire having a standard length of about 185 cm. Aspiration catheter 320 may be about 160 cm in length, although this length can be varied as desired.

Figure 4:
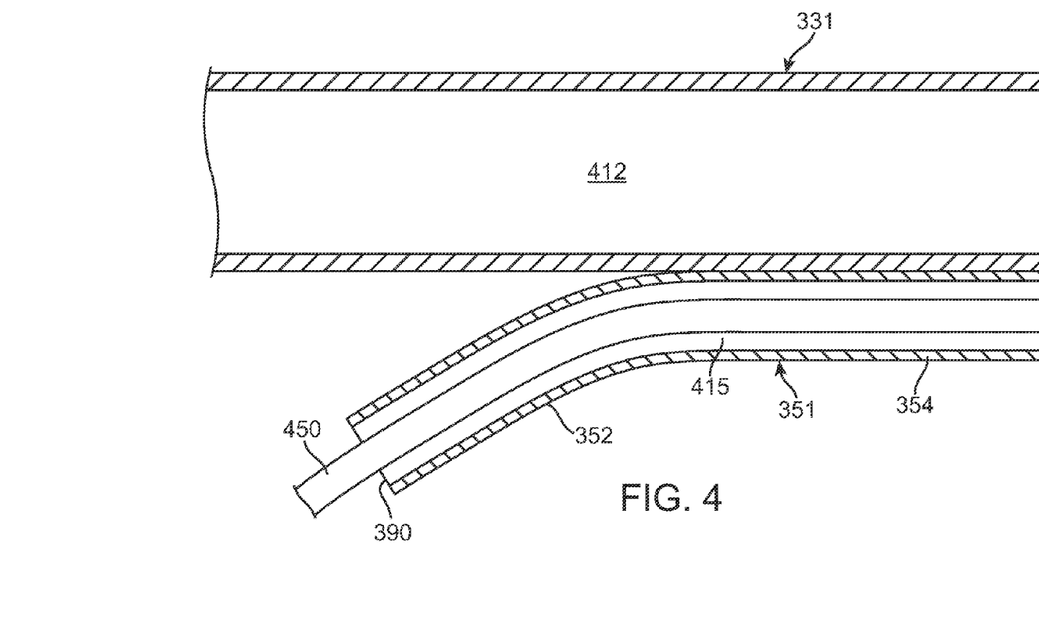
FIG. 4 is an enlarged longitudinal cross-sectional view of a strain relief segment of the aspiration catheter of FIG. 3 in accordance with an embodiment of the present invention, with a guidewire extending within the guidewire lumen.

As shown in FIGS. 3-4, a relatively short, proximal portion of guidewire tube 351 that includes open proximal end 390 is detached from and independent of the outer surface of aspiration tube 331. This detached proximal portion defines a strain relief segment 352. In various embodiments, guidewire tube 351 may have a length of approximately 10-30 cm. In an embodiment, strain relief segment 352 may be between 0.50 millimeters and one centimeter in length. In another embodiment, strain relief segment 352 may have a length between 0.5-10% of the total length of guidewire tube 351.

Strain relief segment 352 is shown in FIGS. 3-4 as being curved away from aspiration tube 331 in order to illustrate that strain relief segment 352 is detached from aspiration tube 331. However, as explained in more detail with reference to FIGS. 5-6, strain relief segment 352 lies generally parallel with and adjacent to aspiration tube 331 when no forces are applied thereto. A distal portion 354 of guidewire tube 351 is attached to the outer surface of aspiration tube 331. In the embodiment depicted in FIG. 3, a relatively short, distal end 356 of guidewire tube 351 that includes distal opening 329 extends beyond second fluid port 324 of aspiration tube 331 to define distal tip 326 of catheter 320. However, it will be understood by one of ordinary skill in the art that aspiration tube 331 may extend beyond distal opening 329 of guidewire tube 351 such that the distal end of aspiration tube 331 defines the distal tip of the aspiration catheter. Further, aspiration tube 331 and guidewire tube 351 may extend to the same distal point such that the distal ends of both tubes define the distal tip of the aspiration catheter.

Figure 5:
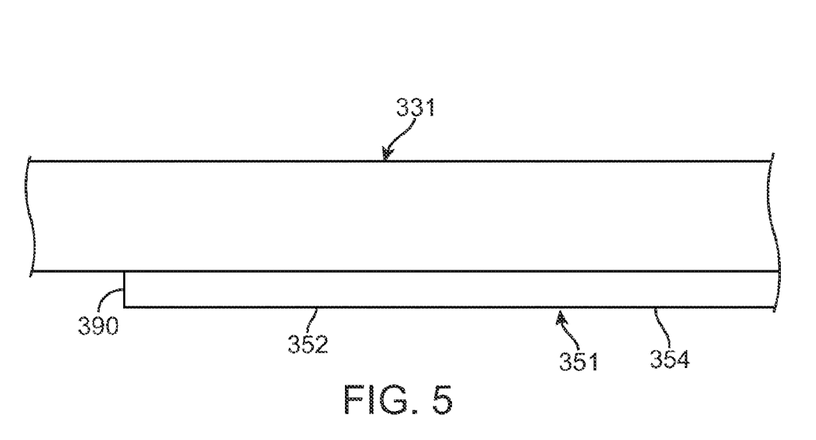
FIG. 5 is an illustration of a strain relief segment according to an embodiment of the present invention, without a guidewire extending through the guidewire lumen.

FIG. 5 is an illustration of detached strain relief segment 352 with no forces applied thereto and without a guidewire extending through guidewire lumen 415. As shown in FIG. 5, strain relief segment 352 lies generally parallel with and adjacent to aspiration tube 331. However, strain relief segment 352 is not attached to aspiration tube 331. Detached strain relief segment 352 is made from a flexible material such that it can fold distally over distal portion 354 of guidewire tube 351, which is attached to aspiration tube 331, as shown, for example, in FIG. 11. Folded strain relief segment 352 may be tracked along a vessel wall 1158 of a body lumen 1159 without causing damage to the tissue if aspiration catheter 320 is withdrawn through the vessel without a guidewire.

Figure 6:
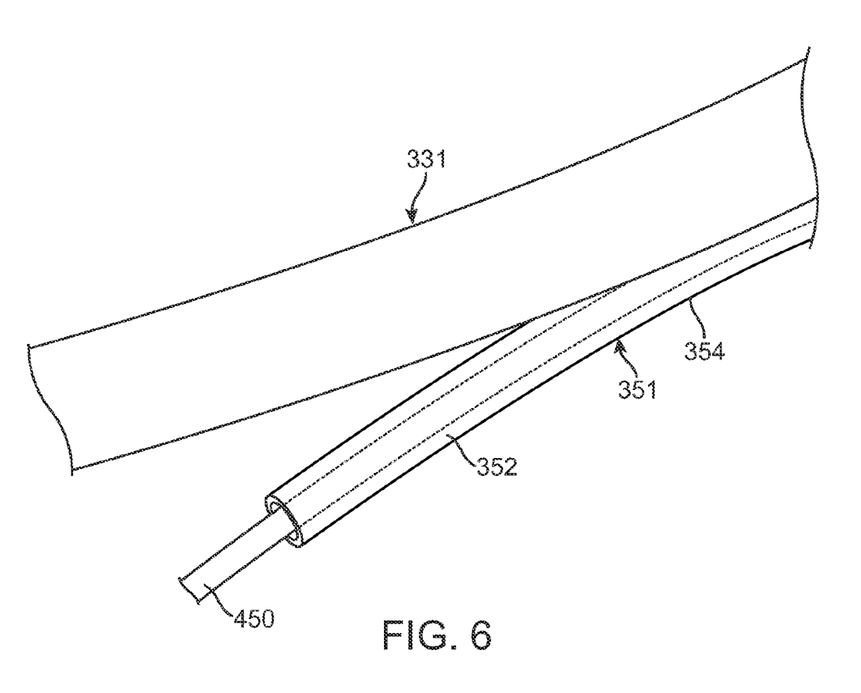
FIG. 6 is an illustration of the strain relief segment shown in FIG. 5, with a guidewire extending within the guidewire lumen.

FIG. 6 is an illustration of detached strain relief segment 352 with guidewire 450 extending through guidewire lumen 415. As can be seen from FIG. 6, guidewire 450 may apply forces to guidewire tube 351 that cause strain relief segment 352 to extend away from the outer surface of aspiration tube 331. As shown, when such transverse force is applied to spread guidewire 450 away from the catheter, then strain relief segment 352 is no longer generally parallel with or adjacent to aspiration tube 331. The transverse force applied by guidewire 450 attempts to separate or rip distal portion 354 of guidewire tube 351 from aspiration tube 331. However, the strength of the attachment between distal portion 354 of guidewire tube 351 and aspiration tube 331 is strong enough to resist the peeling force applied by guidewire 450 under the expected clinical conditions.

Figure 7:
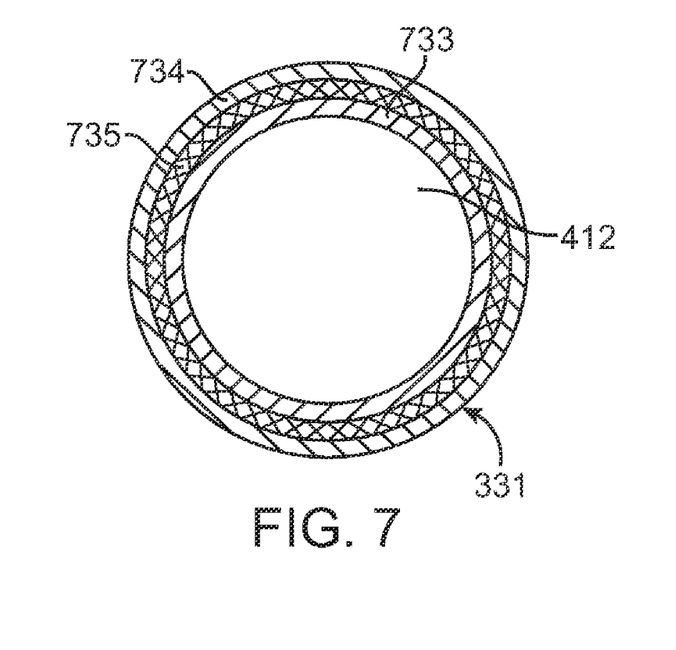
FIG. 7 is a transverse cross sectional view of an aspiration catheter in accordance with the present invention taken along line 7-7 in FIG. 3.

FIG. 7 is a transverse cross-sectional view of aspiration tube 331 taken along line 7-7 in FIG. 3. The tubular wall of aspiration tube 331 includes an outer jacket 734 adhered about an inner liner 733 with a reinforcement layer 735 interposed therebetween. Aspiration tube 331 defines open aspiration lumen 412 along a length thereof as described above. As shown in FIG. 7, the transverse cross-section of aspiration tube 331 is generally circular in shape. In an embodiment, aspiration lumen 412 may have a diameter of about 1.143 mm (0.045 inch).

Inner liner 733 and outer jacket 734 may be made from thermoplastic resins that are the same or are at least chemically compatible to permit thermal (melt) or solvent bonding between liner 733 and jacket 734 through the interstices of reinforcement layer 735. Examples of suitable thermoplastic resins include amides, polyamides, polyethylene block amide copolymers (PEBA), polyurethanes, and polyolefins such as polyethylenes or polypropylene. Alternatively, inner liner 733 and outer jacket 734 may be incompatible for melt bonding, but can be adhesively bonded together through the interstices of reinforcement layer 735.

Reinforcement layer 735 can be formed from a braided or coiled filament of stainless steel, work-hardenable nickel-cobalt based superalloy, platinum alloy, refractory metal alloy such as tungsten or tantalum, or a combination thereof. The filaments of reinforcement layer 735 may have a cross-section that is round, oval, flat, or rectangular. The distal region of elongate tubular body 321 is preferably more flexible than the proximal region, and this can be achieved by providing a braid or coil density at the distal end that is greater than the braid or coil density at the proximal end. The braid or coil of reinforcement layer 735 has sufficiently large coil spacing or braid interstices to permit liner 733 and jacket 734 to be secured together therethrough. In an embodiment, reinforcement layer 735 comprises a braid of flat stainless steel wire measuring 0.038 mm (0.0015 inch) wide and 0.013 mm (0.0005 inch) thick, the braid having a pick count that varies from about 45 picks per longitudinal inch along the catheter proximal region to about 70 picks per longitudinal inch along the catheter distal region. Pick, or pic, is a term well known to one of skill in the art of catheters and refers to the intersection or crossing of two filaments in a woven tubular braid.

Figure 8:
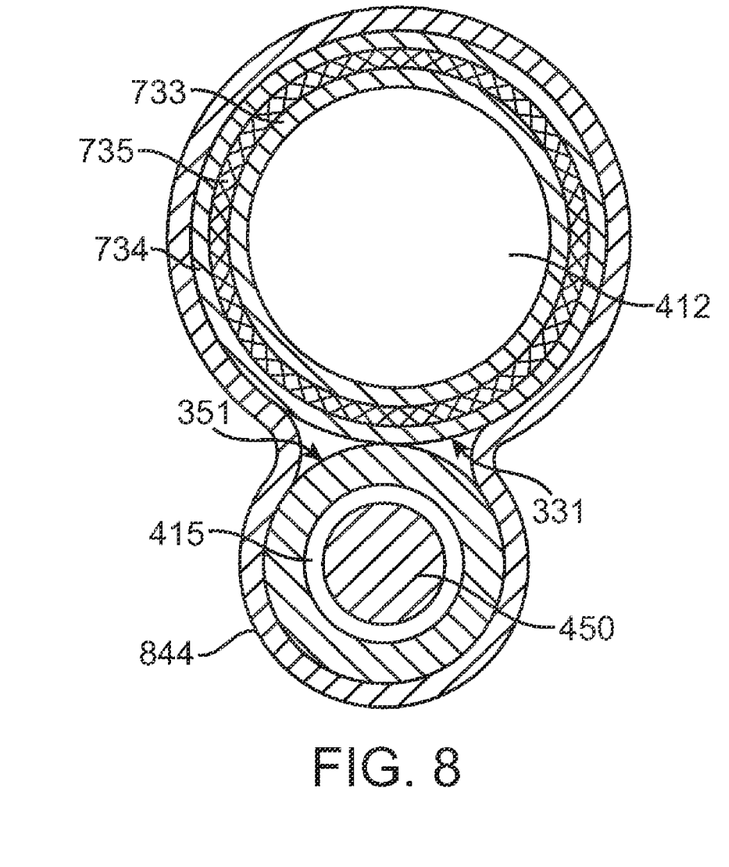
FIG. 8 is a transverse cross sectional view of an aspiration catheter in accordance with the present invention taken along line 8-8 in FIG. 3.

FIG. 8 is a transverse cross-sectional view of dual lumen section 341 of aspiration catheter 320 taken along line 8-8 in FIG. 3. Aspiration lumen 412 defined by aspiration tube 331 and guidewire lumen 415 defined by guidewire tube 351 are in a parallel or side-by-side configuration. Guidewire 450 is shown within guidewire lumen 415 in FIG. 8, but not in FIG. 3. In various embodiments, the diameter of guidewire lumen 415 may range from about 0.381 mm (0.015 inch) to about 0.508 mm (0.020 inch) for receiving medical guidewire 450. Within dual lumen section 341, an over sleeve 844 surrounds and secures together guidewire tube 351 and aspiration tube 331. Over sleeve 844 may also be made of suitable thermoplastic resins such as amides, polyamides, PEBA, polyurethanes, and polyolefins such as polyethylenes or polypropylenes. The material for outer sleeve 844 may be the same as or may at least be chemically compatible with jacket 734 of aspiration tube 331 to be thermally or solvent bonded thereto. In an embodiment, jacket 734 is made of polyamide, and over sleeve 844 is made of 40D durometer PEBA.

In another embodiment (not shown), outer jacket 734 of aspiration tube 331 may be removed from the portion of aspiration tube 331 within dual lumen section 341. Outer jacket 734 may be selectively removed from aspiration tube 331 by a laser ablation process disclosed in U.S. Pat. No. 6,059,769, which is incorporated by reference herein in its entirety. Over sleeve 844 can be shrunk and molded into place around guidewire tube 351 and the altered portion of aspiration tube 331 using removable shrink tubing as a tool, similar to the technique described in the '769 patent. In yet another embodiment (not shown), outer jacket 734 is removed from a section of aspiration tube 331 proximal to dual lumen section 341. As described in the '769 patent, the removed portion of outer jacket 734 can be replaced with a filler material having a different flexibility to advantageously vary the stiffness along elongate tubular body 321. An additional section of over sleeve 844 or an alternative polymer resin may be used as the filler material.

The elongate catheter shaft must have sufficient structural integrity, or "stiffness," to permit the catheter to be pushed through the vasculature to remote arterial locations without buckling or undesirable bending of the catheter body. It is also desirable, however, for the catheter body to be fairly flexible near its distal end, so that the catheter may be navigated through tortuous blood vessels. To provide free-sliding movement over a medical guidewire, guidewire tube 351 may be fabricated from flexible low-friction polymers such as polytetrafluoroethylene (PTFE) or a polyolefin. Alternatively, guidewire tube 351 may be made from a polymer selected without regard to its friction properties, and a slippery coating (not shown) can be applied to lumen 415 to reduce friction against a guidewire.

Aspiration catheter 320 is constructed by providing a first elongate flexible tube such as aspiration tube 331 having reinforcement layer 735 encapsulated within a wall of the tube. Aspiration tube 331 has only one lumen such as aspiration lumen 412 extending therethrough. Aspiration tube 331 may be constructed by a reel-to-reel process such as extruding inner liner 733, braiding reinforcement layer 735 around liner 733, and extruding jacket 734 over reinforcement layer 735, as disclosed in the '769 patent discussed above. Other well-known methods may be used to make the laminated structure of aspiration tube 331. A second elongate flexible tube that is substantially shorter than the first elongate flexible tube such as guidewire tube 351 is provided having lumen 415 extending longitudinally therethrough. Guidewire tube 351 may be made from paste-extruded PTFE or from a melt-extruded thermoplastic as mentioned above.

Leaving a relatively short proximal portion of the second tube such as guidewire tube 351 detached from the first tube such as aspiration tube 331 to define a strain relief segment 352, the remaining length of the second tube is secured alongside the first tube using a securement means selected from an adhesive, a solvent bond, thermal bonding, and/or an over sleeve 844 surrounding guidewire tube 351 and aspiration tube 331. Optionally, before securing the second elongate flexible tube alongside the first tube, jacket 734 may be removed from at least a longitudinal portion of the first tube that is to be secured to the second tube. Selectively removing jacket 734 reduces the outside dimensions of aspiration catheter 320 by eliminating one lamination layer. If jacket 734 is removed, then guidewire tube 351 is secured directly to reinforcement layer 735 and, through the interstices of layer 735, to liner 733. Soft catheter tip 326 can be the distal end of guidewire tube 351, or can be a separate component that is molded onto or otherwise secured at the distal end of catheter 320 at any desired step of the manufacturing process.

If thermal bonding is utilized as the securement means, guidewire tube 351 is formed from a material that has a high thermal bonding ability so as to form a strong thermal bond between guidewire tube distal portion 354 and aspiration tube 331. For example, guidewire tube 351 may be formed from suitable thermoplastic resins such as amides, polyamides, PEBA, polyurethanes, and polyolefins such as polyethylenes or polypropylenes. If desired, a slippery coating can be applied to lumen 415 to reduce friction against a guidewire. A thermal bond may be formed between guidewire tube 351 and aspiration tube 331 by utilizing removable heat shrink tubing as a tool, similar to the technique described in the '769 patent. The heat shrink tubing is removed after guidewire tube 351 and aspiration tube 331 are bonded together. Similarly, if over sleeve 844 is utilized as the securement means, over sleeve 844 can be shrunk and molded into place around guidewire tube 351 and aspiration tube 331 using removable shrink tubing as a tool, similar to the technique described in the '769 patent.

In an alternative embodiment of single operator aspiration catheter 320, the securement means between guidewire tube distal portion 354 and aspiration tube 331 is the simultaneous and contiguous formation of guidewire tube 351 and aspiration tube 331 in a unitary two-lumen extrusion. An extruded two lumen precursor shaft can be made of suitable thermoplastic resins as described above, using a continuous thermoplastic extrusion process to create pieces of tubing that are cut to the desired length for an aspiration catheter. Alternatively, the extruded two lumen precursor shaft can be made of non thermoplastic resin such as PTFE using a cold, paste extrusion process. To create the aspiration catheter embodiment shown in FIG. 3, guidewire tube 351 can be formed by removing material that is collinear with guidewire tube 351 and proximal to dual lumen section 341. Similarly, distal tip 326 can be formed by removing material that is collinear with aspiration tube 331 and distal to second fluid port 324. Strain relief segment 352 can be formed by cutting between aspiration lumen 412 and guidewire lumen 415 to form a relatively short, proximal portion of guidewire tube 351 that it is detached from and independent of aspiration tube 331. Cutting and/or removal of material to form single operator aspiration catheter 320 from an extruded two lumen precursor shaft can be done with well known tools such as a sharp blade, a heated wire, a laser beam or other suitable device.

In accordance with alternate embodiments of the present invention, a detachable strain relief segment may be "tacked" or minimally attached to the aspiration tube. "Minimally attached" as used herein is intended to mean that the strain relief segment is attached to the aspiration tube with only enough bond strength or adhesion to hold it adjacent to the aspiration tube, such that the strain relief feature may be activated when a transverse peeling force is applied. If a transverse peeling force above a predetermined amount is applied, the strain relief segment becomes detached from, viz., rips or tears away from, the aspiration tube in order to prevent the above-described problem of the guidewire tearing through the guidewire shaft. If such a transverse peeling force is not applied, the strain relief segment remains attached to the aspiration tube.

Figure 9:
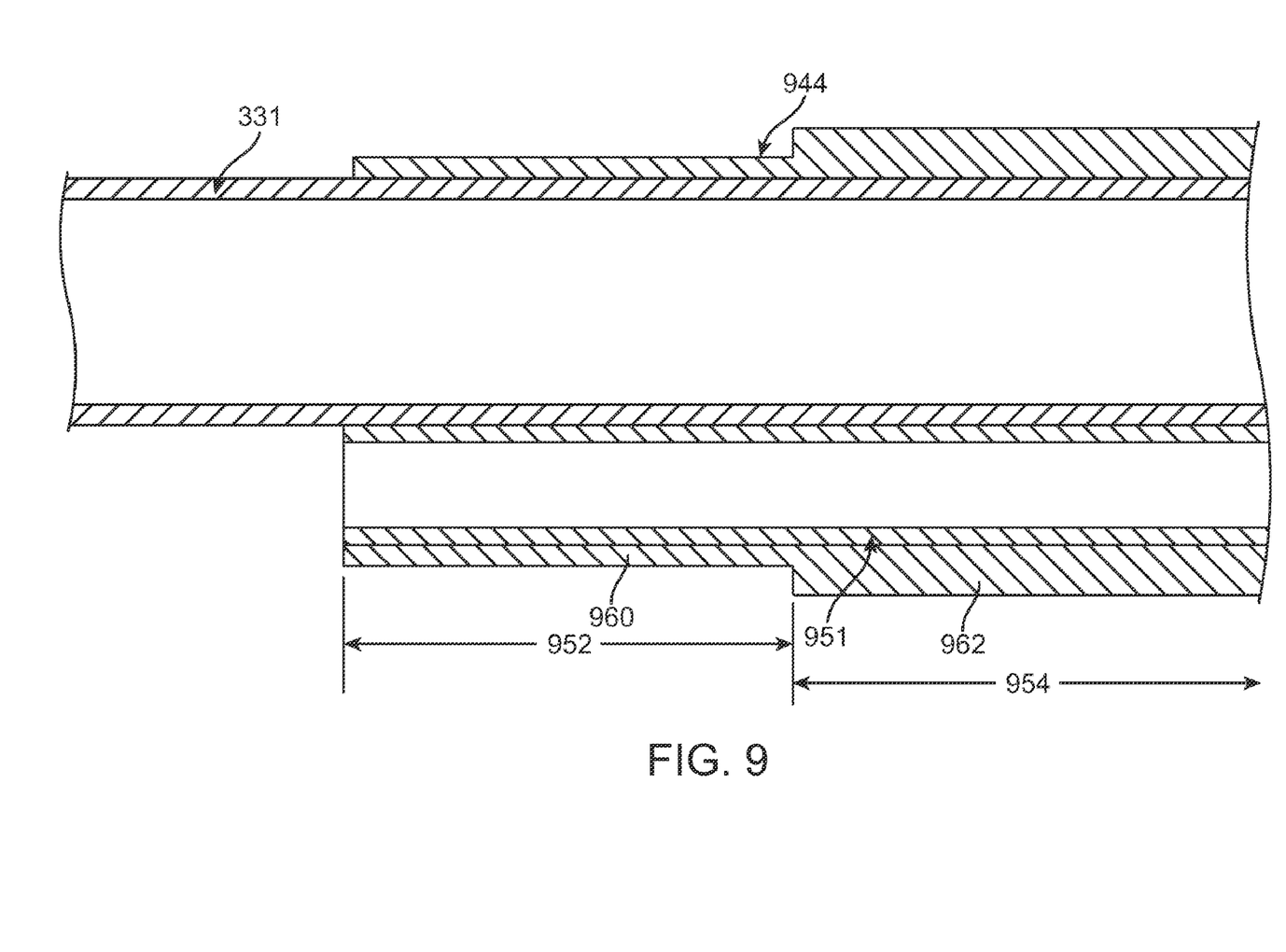
FIG. 9 is an enlarged longitudinal cross-sectional view of a strain relief segment in accordance with another embodiment of the present invention.

More particularly, in an embodiment illustrated in FIG. 9, a guidewire tube 951 includes a minimally attached strain relief segment 952 at a proximal end thereof. Guidewire tube 951 is similar to guidewire tube 351 described above, except that strain relief segment 952 is a short proximal portion of guidewire tube 951 that is minimally attached to the outer surface of aspiration tube 331. In an embodiment, strain relief segment 952 may be between 0.50 millimeters and one centimeter in length, or may have a length between 0.5-10% of the total length of guidewire tube 951. The remaining distal portion 954 of guidewire tube 951 is securely attached to the outer surface of aspiration tube 331. When a guidewire extends through guidewire tube 951, the guidewire may apply a transverse peeling force to guidewire tube 951 that is sufficient to cause strain relief segment 952 to become detached from and subsequently extend away from the outer surface of aspiration tube 331. The transverse force applied by the guidewire does not separate or rip distal portion 954 of guidewire tube 951 from aspiration tube 331, because the attachment between distal portion 954 of guidewire tube 951 and aspiration tube 331 is strong enough to resist the peeling force applied by the guidewire under the expected clinical conditions.

In order to minimally attach strain relief segment 952 to aspiration tube 331, an over sleeve 944 having a reduced wall thickness in the strain relief region may be used. Over sleeve 944 surrounds and secures guidewire tube 951 and aspiration tube 331. Over sleeve 944 includes a proximal portion 960 and a distal portion 962. Over sleeve proximal portion 960 has a first thickness, and over sleeve distal portion 962 has a second thickness that is greater than the first thickness. Proximal portion 960 overlays strain relief segment 952, while distal portion 962 overlays distal portion 954 of guidewire tube 951. When no forces are applied, relatively thin proximal portion 960 of over sleeve 944 holds strain relief segment 952 against aspiration tube 331. However, if transverse forces are applied to guidewire tube 951 by the guidewire, proximal portion 960 will split apart to allow strain relief segment 952 to become detached from aspiration tube 331. In contrast, the relatively thicker distal portion 962 of over sleeve 944 remains intact and continues to secure guidewire tube distal portion 954 to aspiration tube 330.

Over sleeve proximal portion 960 may be formed by displacing the material of over sleeve 944 during assembly of the catheter components. Over sleeve 944 may be shrunk and molded into place around guidewire tube 951 and aspiration tube 331, such as by using a removable heat shrink tubing similar to the technique described in the '769 patent. Over sleeve 944 may be made of suitable thermoplastic resins such as amides, polyamides, PEBA, polyurethanes, and polyolefins such as polyethylenes or polypropylenes. During the heat shrinking operation, the material of over sleeve 944 will flow in response to the thermal parameters and movement relative to the heat source. Thus, by controlling the heat source, the thickness of the material in the strain relief region may be thermally reduced.

Figure 10:
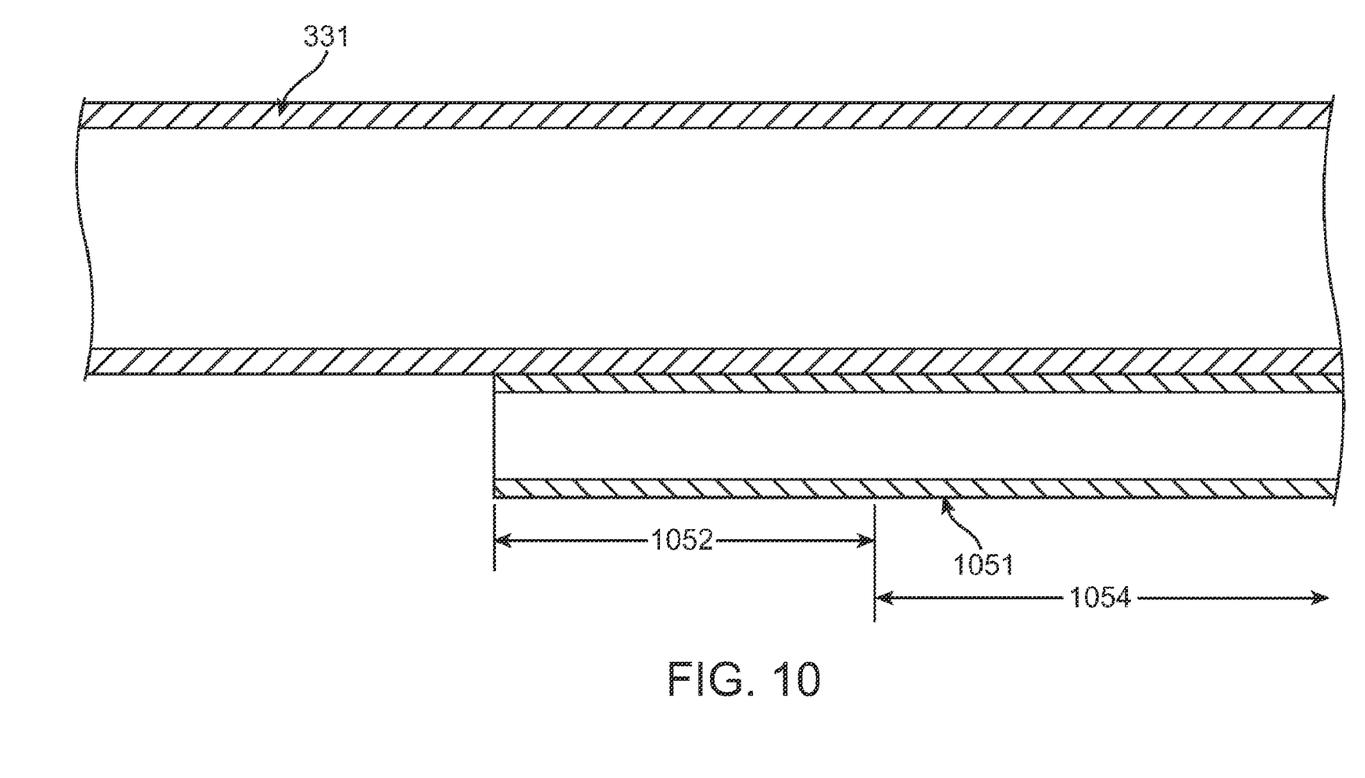
FIG. 10 is an enlarged longitudinal cross-sectional view of a strain relief segment in accordance with another embodiment of the present invention.
Figure 11:
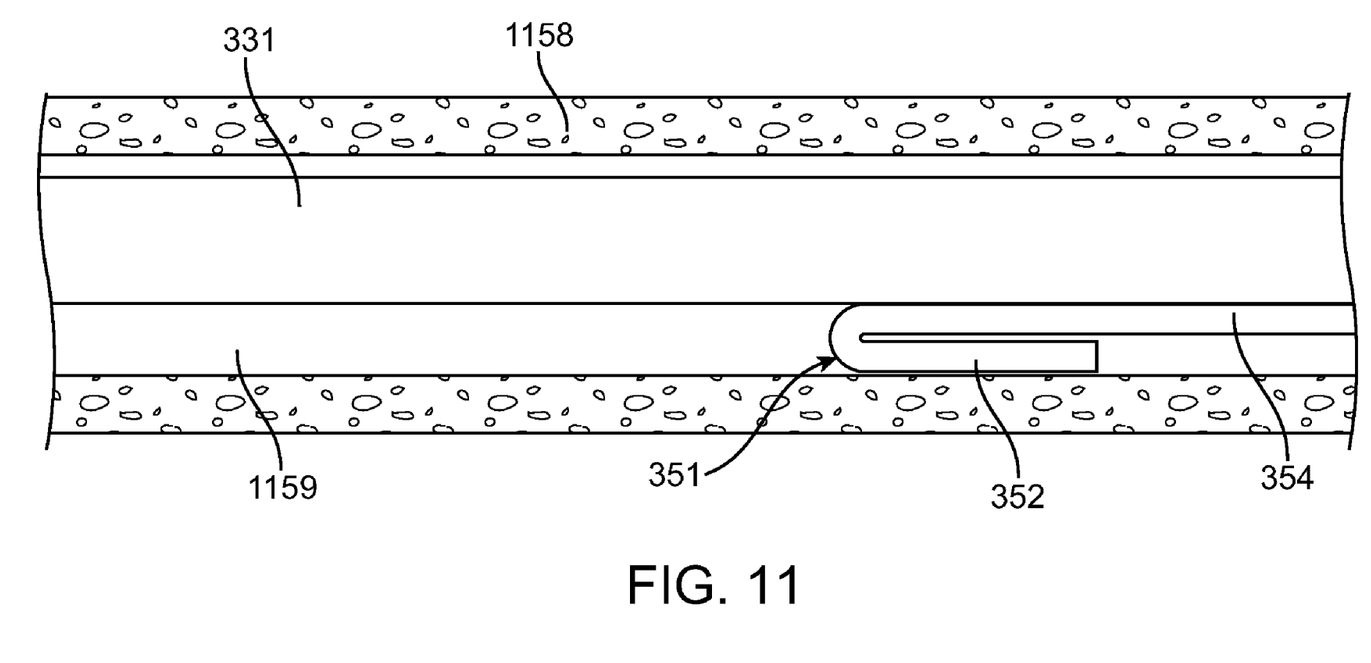
FIG. 11 is an illustration of the strain relief segment shown in FIG. 5 as the aspiration catheter is withdrawn from a body lumen.

Another embodiment for minimally attaching the strain relief segment of the guidewire tube to the aspiration tube is illustrated in FIG. 10. A guidewire tube 1051 of PTFE includes a strain relief segment 1052 at a proximal end thereof, wherein strain relief segment 1052 is a short proximal portion of guidewire tube 1051 that is minimally attached to the outer surface of aspiration tube 331 by using a thermal bond. The thermal bonding ability of PTFE is relatively poor, thus resulting in a minimal or weak bond between strain relief segment 1052 and aspiration tube 331. When no forces are applied, the thermal bond holds strain relief segment 1052 against aspiration tube 331. However, if transverse forces are applied to guidewire tube 1051 by the guidewire, the thermal bond may be broken to allow strain relief segment 1052 to become detached from aspiration tube 331. The remaining distal portion 1054 of guidewire tube 1051 is securely attached to the outer surface of aspiration tube 331 by an adhesive, a solvent bond, and/or an over sleeve, as discussed in previous embodiments, such that in contrast, distal portion 1054 remains secured alongside aspiration tube 330 despite any forces applied thereto.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An aspiration catheter for removing particles from a blood vessel, the catheter comprising:
an elongate aspiration tube having an aspiration lumen defined by an inner surface of the aspiration tube, the aspiration tube having a proximal end port and a distal end port fluidly connected via the aspiration lumen; and
a guidewire tube disposed alongside and not extending proximally beyond a distal portion of the aspiration tube, the guidewire tube having a guidewire lumen defined by an inner surface of the guidewire tube and having a proximal end opening and a distal end opening that are connected via the guidewire lumen,
wherein the guidewire tube includes a distal portion in contact with and directly secured to the distal portion of the aspiration tube and a proximal portion defining a detachable strain relief segment that is minimally attached to the distal portion of the aspiration tube, such that a transverse force applied to the guidewire tube transversely detaches only the strain relief segment of the guidewire tube from the aspiration tube.

2. The aspiration catheter of claim 1, wherein the guidewire tube is secured to the aspiration tube by an over sleeve that surrounds the guidewire tube and the aspiration tube, the over sleeve having a proximal portion of a first thickness that overlays the strain relief segment and a distal portion of a second thickness that overlays the distal portion of the guidewire tube, the second thickness being greater than the first thickness.

3. The aspiration catheter of claim 1, wherein the guidewire tube is made from PTFE and the strain relief segment is minimally attached to the aspiration tube by a thermal bond, wherein the thermal bond is broken when the transverse force is applied thereto.

4. The aspiration catheter of claim 1, wherein the guidewire tube has a length of 10-30 cm.

5. The aspiration catheter of claim 1, wherein the length of the strain relief segment is 0.5-10% of the length of the guidewire tube.

6. The aspiration catheter of claim 1, wherein the distal portion of the guidewire tube is secured to the aspiration tube by a securement means selected from a group consisting of an adhesive, a solvent bond, thermal bonding, and an over sleeve that surrounds the distal portion of the guidewire tube and the aspiration tube.

7. The aspiration catheter of claim 1, wherein the aspiration tube further comprises:
a reinforcement layer encapsulated within a wall of the aspiration tube.

8. The aspiration catheter of claim 7, wherein the aspiration tube further comprises:
a liner having an inner surface defining the aspiration lumen; and
a jacket disposed about and adhered to the liner, wherein the reinforcement layer is interposed between the jacket and the liner.

9. The aspiration catheter of claim 7, wherein the reinforcement layer comprises a tubular braid.

10. The aspiration catheter of claim 1, wherein the distal port of the aspiration tube forms an oblique opening that faces away from the guidewire tube.

11. The aspiration catheter of claim 1, further comprising:
a fitting mounted to a proximal end of the aspiration tube in fluid communication with the proximal port.

* * * * *